United States Patent [19]

Chang

[11] Patent Number: 5,254,671
[45] Date of Patent: Oct. 19, 1993

[54] EXTRACELLULAR SEGMENTS OF HUMAN E IMMUNOGLOBULIN ANCHORING PEPTIDES AND ANTIBODIES SPECIFIC THEREFOR

[75] Inventor: Tse W. Chang, Houston, Tex.

[73] Assignee: Tanox Biosystems, Inc., Houston, Tex.

[21] Appl. No.: 973,321

[22] Filed: Oct. 29, 1992

Related U.S. Application Data

[63] Continuation-in-part of Ser. No. 515,604, Apr. 27, 1990, abandoned.

[51] Int. Cl.$^5$ .......................... C07K 7/10; C12N 15/13
[52] U.S. Cl. .................................... 530/324; 530/350; 530/386; 536/23.53
[58] Field of Search .......................... 536/23.23, 23.53; 530/324, 350, 386

[56] References Cited

FOREIGN PATENT DOCUMENTS

WO89/06138 7/1989 PCT Int'l Appl.

OTHER PUBLICATIONS

Sun, L K et al. Transfectomas expressing both secreted and membrane-bound forms of chimeric IgE with anti--viral specificity. Journal of Immunology. 146:199–205, 1991.

Chang, T W et al. Monoclonal antibodies specific for human IgE-producing B cells: a potential therapeutic for IgE-mediated allergic diseass. Bio/Technology 8:122–126, 1990.

EPO Search Report.

*Primary Examiner*—Y. Christina Chan
*Assistant Examiner*—F. C. Eisenchenk
*Attorney, Agent, or Firm*—Eric P. Mirabel

[57] ABSTRACT

Antigenic epitopes associated with the extracellular segment of the domain which anchors immunoglobulins to the B cell membrane are disclosed. For IgE, the epitopes are present on IgE-bearing B cells but not basophils or the secreted, soluble form of IgE. The epitope can be exploited for therapy and diagnosis. For example, antibodies or immunotoxins specific for the epitopes associated with the anchor domain of IgE can be used to selectively destroy or downregulate IgE-bearing lymphocytes, thus blocking IgE-mediated allergic reactions. Three different isoforms of the C-terminal segment of the human ε chain resulting from alternative mRNA splicings in the membrane exon region are disclosed, one of which is secreted and not membrane-bound.

3 Claims, No Drawings

5,254,671

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 216 nucleotides
        ( B ) TYPE: nucleic acid
        ( C ) STRANDEDNESS: double stranded
        ( D ) TOPOLOGY: linear ( x i ) SEQUENCE DESCRIPTION: SEQ ID NO:1:

```
GTA  AAT  CCC  GAG  CTG  GAC  GTG  TGC  GTG        27
Val  Asn  Pro  Glu  Leu  Asp  Val  Cys  Val
1                   5

GAG  GAG  GCC  GAG  GGC  GAG  GCG  CCG  TGG  ACG   57
Glu  Glu  Ala  Glu  Gly  Glu  Ala  Pro  Trp  Thr
10                       15

TGG  ACC  GGC  CTC  TGC  ATC  TTC  GCC  GCA  CTC   87
Trp  Thr  Gly  Leu  Cys  Ile  Phe  Ala  Ala  Leu
20                       25

TTC  CTG  CTC  AGC  GTG  AGC  TAC  AGC  GCC  GCC   127
Phe  Leu  Leu  Ser  Val  Ser  Tyr  Ser  Ala  Ala
30                       35

CTC  ACG  CTC  CTC  ATG  GTG  CAG  CGG  TTC  CTC   157
Leu  Thr  Leu  Leu  Met  Val  Gln  Arg  Phe  Leu
40                       45

TCA  GCC  ACG  CGG  CAG  GGG  AGG  CCC  CAG  ACC   187
Ser  Ala  Thr  Arg  Gln  Gly  Arg  Pro  Gln  Thr
50                       55

TCC  CTC  GAC  TAC  ACC  AAC  GTC  CTC  CAG  CCC   207
Ser  Leu  Asp  Tyr  Thr  Asn  Val  Leu  Gln  Pro
60                       65

CAC  GCC  TAG  216
His  Ala
70
```

( 2 ) INFORMATION FOR SEQ ID NO:2:

( i ) SEQUENCE CHARACTERISTICS:
        ( A ) LENGTH: 166 nucleotides
        ( B ) TYPE: nucleic acid
        ( C ) STRANDEDNESS: double stranded
        ( D ) TOPOLOGY: linear ( x i ) SEQUENCE DESCRIPTION: SEQ ID NO:2:

```
GTA  AAT  CCC  GGG  CTG  GCT  GGC  GGC  TCC  GCG   30
Val  Asn  Pro  Gly  Leu  Ala  Gly  Gly  Ser  Ala
1                   5                        10

CAG  TCC  CAG  AGG  GCC  CCG  GAT  AGG  GTG  CTC   60
Gln  Ser  Gln  Arg  Ala  Pro  Asp  Arg  Val  Leu
              15                             20
```

```
TGC CAC TCC GGA CAG CAG CAG GGA CTG CCG         90
Cys His Ser Gly Gln Gln Gln Gly Leu Pro
                    25                      30

AGA GCA GCA GGA GGC TCT GTC CCC CAC CCC        120
Arg Ala Ala Gly Gly Ser Val Pro His Pro
                35                      40

CGC TGC CAC TGT GGA GCC GGG AGG GCT GAC        150
Arg Cys His Cys Gly Ala Gly Arg Ala Asp
                45                      50

TGG CCA GGT CCC CCA G                          166
Trp Pro Gly Pro Pro
            55
```

(2) INFORMATION FOR SEQ ID NO:3:

(i) SEQUENCE CHARACTERISTICS:
        (A) LENGTH: 591 nucleotides
        (B) TYPE: nucleic acid
        (C) STRANDEDNESS: double stranded
        (D) TOPOLOGY: linear (xi) SEQUENCE DESCRIPTION: SEQ ID NO:3:

```
GAG GCA GCG AGC CCC TCA CAG ACC GTC CAG CGA GCG GTG TCT GTA         45
Glu Ala Ala Ser Pro Ser Gln Thr Val Gln Arg Ala Val Ser Val
1               5                   10                  15

AAT CCC GGT GCA GCG GTT CCT CTC AGC CAC GCG GCA GGG GAG GCC CCA    93
Asn Pro Gly Ala Ala Val Pro Leu Ser His Ala Ala Gly Glu Ala Pro
            20                  25                  30

GAC CTC CCT CGA CTA CAC CAA CGT CCT CCA GCC CCA CGC CTA GGC CGC    141
Asp Leu Pro Arg Leu His Gln Arg Pro Pro Ala Pro Arg Leu Gly Arg
            35                  40                      45

GGG CCA CTC ACG CTC CAC CAG GCC CAG CTT TTT CTC TGC CAG CGC CTG    189
Gly Pro Leu Thr Leu His Gln Ala Gln Leu Phe Leu Cys Gln Arg Leu
        50                  55                  60

AGC CTC CCT CGG GCT GCA CCC TGC CCT GGG TGG GAA AAG GGA AGC AGA    237
Ser Leu Pro Arg Ala Ala Pro Cys Pro Gly Trp Glu Lys Gly Ser Arg
    65                  70                  75

CAA GAA AAG GGG GCA CAA GGT CAC TAC TGT GGG CTG ATG GCC AGT        282
Gln Glu Lys Gly Ala Gln Gly His Tyr Cys Gly Leu Met Ala Ser
80                  85                  90

GAA CCT GAG CCC AGA GGG GCC GGC TCA GCC GCA AGG TTA CAG GCG        327
Glu Pro Glu Pro Arg Gly Ala Gly Ser Ala Ala Arg Leu Gln Ala
95              100                 105

CCG AGA GAA CCA CCA GTC GCA GCC CCC ACC CGA AAA CCG TGT CTG        372
Pro Arg Glu Pro Pro Val Ala Ala Pro Thr Arg Lys Pro Cys Leu
110             115                 120

TCC CTT CAA CAG AGT CAT CGA GGA GGG GTG GCT GCT AGC CGT TCT        417
Ser Leu Gln Gln Ser His Arg Gly Gly Val Ala Ala Ser Arg Ser
125             130                 135

GAG CTC ATC CCA GGC CCC TGG GTC TCC GGG TCA CTC CCA TTC            459
Glu Leu Ile Pro Gly Pro Trp Val Ser Gly Ser Leu Pro Phe
140                 145                 150

TGACTGTACA ATCACCAAAA GCCAAGGAGG GCCCGGCACC AGCCCAGGGC             509

ACAGCTGAGT CTGCGTCCAG CCCAACACCA GCCCACGGCC TCACTCCCCA             559

GCCTCGGTCT GACCCTTCTA GCCCTGAGAT CC                                591
```

(2) INFORMATION FOR SEQ ID NO:4:

(i) SEQUENCE CHARACTERISTICS:
        (A) LENGTH: 23 nucleotides
        (B) TYPE: nucleic acid
        (C) STRANDEDNESS: single stranded
        (D) TOPOLOGY: linear ( x i ) SEQUENCE DESCRIPTION: SEQ ID NO:4:

GAGGAATTCT CGGTGCAGTG GCT    23

( 2 ) INFORMATION FOR SEQ ID NO:5:

( i ) SEQUENCE CHARACTERISTICS:
        ( A ) LENGTH: 28 nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:5:

GGGAATTCCT GGTGGAGCGT GAGTGGCC    28

( 2 ) INFORMATION FOR SEQ ID NO:6:

( i ) SEQUENCE CHARACTERISTICS:
        ( A ) LENGTH: 29 nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:6:

CAGAATTCAG ATGAGTTCAT CTGCCGTGC    29

( 2 ) INFORMATION FOR SEQ ID NO:7:

( i ) SEQUENCE CHARACTERISTICS:
        ( A ) LENGTH: 28 nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:7:

GCGAATTCGA TGCAGAGGCC GGTCCACG    28

( 2 ) INFORMATION FOR SEQ ID NO:8:

( i ) SEQUENCE CHARACTERISTICS:
        ( A ) LENGTH: 20 nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:8:

AGGGACTGCC GAGAGCAGCA    20

( 2 ) INFORMATION FOR SEQ ID NO:9:

( i ) SEQUENCE CHARACTERISTICS:
        ( A ) LENGTH: 21 nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:9:

CTCGGCAGTC CCTGCTGCTG T    21

( 2 ) INFORMATION FOR SEQ ID NO:10:

( i ) SEQUENCE CHARACTERISTICS:
        ( A ) LENGTH: 33 amino acids
        ( B ) TYPE: amino acid
        ( D ) TOPOLOGY: linear ( x i ) SEQUENCE DESCRIPTION: SEQ ID NO:10:

Ser His Ala Ala Gly Glu Ala Pro Asp Leu Pro Arg Leu His Gln Arg Pro    1
     5                10              15

```
Pro Ala Pro Arg Leu Ala Ala Glu His Ser Arg Ser Thr Arg Pro Ser
     20                  25                  30
```

EXTRACELLULAR SEGMENTS OF HUMAN E IMMUNOGLOBULIN ANCHORING PEPTIDES AND ANTIBODIES SPECIFIC THEREFOR

RELATED APPLICATIONS

This application is a continuation-in-part of U.S. Application Ser. No. 07/515,604, filed Apr. 27, 1990 now abandoned.

BACKGROUND OF THE INVENTION

The immediate-type hypersensitivities, such as extrinsic asthma, hay fever, and allergic responses to certain foods or drugs, are mediated primarily by one of the immunoglobulin isotypes, i.e., IgE. In an IgE-mediated allergic response, the allergen binds to the IgE which is bound to receptors on the surface of mast cells and basophilic leukocytes (basophils). The binding of the allergen causes crosslinking of the surface IgE molecules and hence the underlying receptors for the Fc portion of IgE (FcεR), thereby triggering the release of pharmacologic mediators such as histamine, the slow-reacting substance of anaphylaxis (SRA), and serotonin. The release of these mast cell and basophil products causes the pathological reactions and symptoms of allergy.

IgE is secreted by a particular class of B cells, which also express IgE on their surface. In individuals sensitized to specific allergens, the allergen-specific IgE is continuously produced by these B cells. Nevertheless, individuals who have no secreted IgE in their systems (and no IgE producing B cells) appear to live normally, indicating that IgE is not essential in the immune response. IgE may, however, be useful in fighting infection by parasites.

It seems, therefore, that reducing secreted IgE by suppressing or depleting IgE producing B cells would be a viable therapy for allergy. Monoclonal antibodies (and derivative and related products) which bind specifically to the IgE producing B cells could be used in such a suppression or elimination process. The immune system's regulatory, cytolytic or cytotoxic mechanisms can be used to suppress or destroy cells which are bound by monoclonal antibodies, or by the derivative or related products.

IgE binds to the FcεR receptors on the surface of basophils and mast cells very strongly, with an association constant, Ka, of about $1 \times 10^{10}$ liter/mole. Even though IgE is not synthesized by basophils and mast cells, the very strong and stable association of IgE with FcεR means that IgE is virtually always present and exposed on the surface of these cells. Thus, an immunotherapeutic agent targeting the IgE on B cells must not react with the IgE on basophils and mast cells, in order to avoid cross-linking this IgE and the underlying FcεR and thereby triggering an allergic reaction.

SUMMARY OF THE INVENTION

Immunoglobulins consist of two peptide chains, a heavy chain and a light chain. In IgE, the heavy chain is designated as the ε chain. Membrane anchoring peptides extend from the C terminus of the heavy chains of the immunoglobulins and affix the associated immunoglobulin to the cell membrane surface. These membrane anchoring peptides can be divided into three segments in terms of locations in relation to the plasma membrane. The middle segments have 25 hydrophobic and uncharged amino acid residues, suggesting that they are in the membrane lipid bilayer. The C-terminal hydrophilic segments have 3-28 amino acid residues, suggesting that they are intracellular. The segments toward the N-termini contain about 13 to 67 amino acid residues, and are highly acidic and hydrophilic, suggesting that they are on the extracellular surface of the plasma membrane.

The extracellular segments of these peptides are unique for different isotypes. Therefore, the extracellular segment of the ε chain membrane anchoring peptide forms, in whole or in part, an epitope unique to the B cells which produce IgE. However, this membrane-bound immunoglobulin isotype specific ("migis") extracellular epitope is not present on secreted, soluble IgE (or on IgE bound to the FcεR) because only the IgE which is bound to the surface of B cells contains the membrane anchoring peptide as part of its heavy chain.

The antibodies and other immunotherapeutic agents of the invention bind to the migis epitopes on the surface of IgE-bearing B cells. These B cells can then be eliminated or controlled by a number of immune mechanisms. These antibodies and other immunotherapeutic agents can be used in in vivo or extracorporeal allergy therapy, and in diagnosis, as described further below.

It has been discovered that because of alternative mRNA splicings, there are at least three different nucleotide sequences which encode for peptides in the membrane anchoring region of human ε chain. The deduced amino acid sequences encoded by these three nucleotide sequences are also different, indicating that there are three different isoforms of the human ε chain membrane anchoring peptide.

The deduced amino acid sequence of isoform I shows that it has 67 amino acid residues, and a 15 amino acid peptide segment toward the N-terminus. This 15 amino acid segment is proposed to be extracellular and to form, entirely or in-part, the migis epitope. Isoform II has 119 amino acid residues, 67 of which are towards the N terminus and form the proposed extracellular segment. Isoform III, having 153 amino acid residues, is secreted and does not have a membrane-bound extracellular segment.

DETAILED DESCRIPTION OF THE PREFERRED EMBODIMENTS AND THEIR MANNER AND PROCESS OF MAKING AND USING

1. Migis Epitopes and Their Uses in Therapy and Diagnosis

Membrane-bound immunoglobulins on B cells differ from the secretory, soluble immunoglobulins synthesized by the same B cells in that the former have an extra peptidic piece that anchors them onto the B cell surface. The membrane-bound immunoglobulins on B cells from different species, for which amino acid sequences have been determined, have extra isotype-specific regions that anchor the immunoglobulins to the membrane. These peptidic regions have lengths ranging from 41 to 130 amino acids and can be divided into three segments. There is a middle segment of 25 hydrophobic and uncharged amino acids, which is believed to be located in the cytoplasmic membrane bilayer. There is a C-terminal hydrophilic segment of 3-28 amino acid residues, which is believed to be located on the cytoplasmic side of the membrane. There is a segment toward the N-terminus of about 13 to 67 amino acid residues, which is highly acidic and hydrophilic and proposed to lie on the extracellular surface of the plasma membrane.

The length and the hydrophilic and highly charged nature of the extracellular segment indicate that this segment is exposed and accessible to antibodies. The antigenic epitopes located on the extracellular segment of the membrane-bound region of immunoglobulin heavy chains are designated herein as the migis epitopes. The migis epitopes allow for developing several types of monoclonal or polyclonal antibody-based therapies and diagnoses for IgE-mediated allergic diseases.

2. Membrane Anchoring Peptides of B Cell Membrane-bound Immunoglobulins

The amino acid sequences of ten membrane-bound immunoglobulins from several species have been previously determined by other groups. See Ishida, N. et al., EMBO J., 1:1117 (1982); Steen, M. L. et al., J. Mol. Biol., 177:19-32 (1984); Rogers, J. et al., Cell, 26:19-27 (1981); Yamawaki-Kataoka, Y. et al., Proc. Natl. Acad. Sci., MSA, 79:2008-2012 (1982); Kamaromy, M. et al., Nuc. Acids Res., 11:6775-6785 (1983); Rogers, J. et al., Cell, 20:303-312 (1980); Bernstein, K. E., J. Immunol. 132:490-495 (1984); Cheng, H. et al., Nature, 296:410-415 (1982). These sequences indicate certain common features of the membrane anchoring peptides. As shown in Table 1, and as discussed above, the membrane anchoring peptide has three segments which are distinguishable based upon their locations in relation to the plasma membrane.

TABLE 1

| Key features and properties of membrane anchoring peptides. | | | | |
|---|---|---|---|---|
| Immunoglobulin | Number of Amino Acid Residues | | | |
| Class/Subclass | 1. | 2. | 3. | 4. |
| Mouse IgE2 | 19 | 25 | 28 | 72 |
| Rat IgE | 19 | 25 | 28 | 72 |
| Mouse IgG$_1$ | 18 | 25 | 28 | 71 |
| Mouse IgG$_{2a}$ | 18 | 25 | 28 | 71 |
| Mouse IgG$_{2b}$ | 18 | 25 | 28 | 71 |
| Mouse IgG$_3$ | 18 | 25 | 28 | 71 |
| Mouse IgM | 13 | 25 | 3 | 41 |
| Human IgM | 13 | 25 | 3 | 41 |
| Human IgD | 27 | 25 | 3 | 55 |
| Mouse IgD | 26 | 25 | 3 | 54 |

1. Designates the first (N terminal) segment of the anchoring peptides, which is hydrophilic and highly acidic, and is proposed to lie on the exterior surface of the cell membrane.
2. Designates the middle segment of the anchoring peptides, which is hydrophobic with no charged residues, and is proposed to lie in the membrane lipid bilayer.
3. Designates the last (C terminal) segment of the membrane anchoring peptides, which is hydrophilic and is proposed to lie in the cell cytoplasm.
4. Represents the total number of amino acid residues in each different membrane anchoring peptide shown.

The shortest migis peptides have 13 amino acid residues (mouse and human $\mu$ chains). See Table 1. The migis peptides of all immunoglobulins contain charged and polar hydrophilic amino acid residues. The proportions of charged amino acid residues and polar hydrophilic residues account are high for the various migis peptides (Table 2). Thus, it is proposed that all the migis peptides are exposed and long enough to be accessible by antibodies.

TABLE 2

Composition of charged amino acid residues and polar, hydrophilic amino acid residues of the migis peptides.

| | Acidic residues | Basic residues | Polar residues | hydrophilic residues | Proportion of hydrophilic residues % |
|---|---|---|---|---|---|
| | # Amino acid residues | | | | |
| Mouse IgE | 10 | 0 | 2 | 12 | 63 |

TABLE 2-continued

Composition of charged amino acid residues and polar, hydrophilic amino acid residues of the migis peptides.

| | Acidic residues | Basic residues | Polar residues | hydrophilic residues | Proportion of hydrophilic residues % |
|---|---|---|---|---|---|
| Rat IgE1 | 10 | 0 | 2 | 12 | 63 |
| Mouse IgG$_1$ | 6 | 0 | 4 | 10 | 56 |
| Mouse IgG$_{2a}$ | 7 | 0 | 2 | 9 | 50 |
| Mouse IgG$_{2b}$ | 7 | 1 | 1 | 9 | 50 |
| Mouse IgG$_3$ | 6 | 0 | 4 | 10 | 56 |
| Mouse IgM | 6 | 0 | 2 | 8 | 61 |
| Human IgM | 6 | 0 | 1 | 7 | 54 |
| Human IgD | 6 | 1 | 8 | 15 | 56 |
| Mouse IgD | 7 | 0.5 | 9 | 16.5 | 63 |

Acidic residues: (Glu), (Asp)
Basic residues: (Lys), (Arg), (His); His is partially charged.
Polar residues: (Ser), (Thr), (Cys), (Gln), (Asn)

3. Determining the Amino Acid Sequence of the Human $\epsilon$ Chain migis Peptides.

A number of well established procedures can be applied to determine the DNA sequence corresponding to the human $\epsilon$ chain migis peptides. One approach is to start with the mRNA preparation of a human myeloma cell line which expresses IgE on the surface. SKO-007 cells can be employed for this purpose. With the mRNA preparation, one can establish a cDNA library by employing lambda phage or plasmids as cloning vectors. A preferred method for constructing the cDNA library is with the cDNA Library Construction System Kit-Librarian I developed and commercialized by Invitrogen (San Diego, Calif.). A stepwise detailed instruction manual is provided for RNA isolation from cells, reverse transcription, second strand synthesis, linker ligation, agarose gel sizing of cDNA, electroelution to purify cDNA, vector ligation, and transformation of *E. coli*. The vector used in this library is pCDM8.

In the screening of the cDNA library for clones containing the migis peptides, several probes can be used. The library can be screened with DNA probe A, which is a 1.1 kb long U266 cDNA covering most of length of $\epsilon$ mRNA (no membrane-bound segment). The positive clones, which include both secreted and membrane-bound forms can be distinguished by using additional probes. Probe B is developed by taking advantage of the probable fact that the end of the CH4 domain is truncated in the human $\epsilon$ chain membrane anchoring peptide. The truncation occurs when the gene segments of the CH4 domain and the membrane-bound domain are translocated. The loss of the C-termini also occurs with the membrane bound forms of other immunoglobulins, including $\epsilon$ and $\mu$, which contain CH4 domains. From the published information on the nucleotide sequence of human $\epsilon$. CH4 domain, the most possible splicing donor site is intracodon GT, 71 bp 5' of the termination codon TGA. Another GT, which is not intracodon and less likely a splicing donor site, is closer to the terminus (24 bp 5' to the termination codon).

Probe B will react with the secreted form of the $\epsilon$ chain gene and not the membrane-bound form of $\epsilon$ chain gene.

The design of probe C was based on the finding that the transmembrane segment of the membrane anchoring peptides is very conserved among all the immunoglobulin genes so far sequenced. There is a segment of peptide and corresponding coding DNA within this transmembrane segment that is nearly identical among all immunoglobulins. The consensus DNA sequence with the eight combinations was used as probe C.

Probe D which represents a segment upstream of the most probable splicing donor site, GT, consists of 36 bp. This probe should react with ε chain gene of both the secreted and membrane-bound forms.

Table 3 summarizes the pattern of reactivities of clones containing ε genes of secreted or membrane-bound forms with the four probes.

TABLE 3

The reactivity of ε gene-containing cDNA clones with probes A, B, C, and D.

|  | ε Secreted | ε Membrane-bound |
| --- | --- | --- |
| Probe A | + | + |
| Probe B | + | − |
| Probe C | − | + |
| Probe D | + | + |

The library size needed to clone the membrane-bound ε chain depends on how abundant the mRNA is. Assuming secreted IgE comprises 0.1% of the SKO-007 poly A+ RNA, the library size should be about 5,000 independent recombinant clones to have a 99% probability to isolate a positive clone. In IgE-producing rat immunocytoma IR2 and IR162 cells, mRNA for the membrane-bound form of ε chain was found to be more than 2% of that of the secreted form. Assuming this ratio of membrane-bound/secreted forms of ε chain holds true for the human IgE-producing SKO-007 cells, the cDNA library size needed to isolate the membrane-bound ε chain is about 250,000. In a preferred procedure, a larger number of clones (about 1,000,000) are screened.

An alternative to the conventional approach of establishing a cDNA library and screening the clones representing the cellular mRNA species is to amplify the mRNA to produce high proportions of their corresponding DNA. The resulting DNA can then be purified by gel electrophoresis and then subjected to sequence analysis. The methodology, referred to as polymerase chain reaction (PCR) amplification, has been established in the past few years and complete systems including reagents and equipment have been commercialized. One preferred system is provided by Perkin Elmer Cetus (Norwalk, Conn.), and includes the GeneAmp DNA Amplification Reagent Kit and the DNA Thermal Cycler.

Some of the specific reagents used in this approach are the same as used for the cDNA library cloning. Since no sequence of the ε chain membrane anchoring peptide has been determined, the strategy is to amplify both the secreted and membrane-bound forms of ε chains. Two primers are to be used, one is oligo.dT (25-30-mers) and one is the oligomer corresponding to probe D. Probe D is located 5′ to the most probable splicing donor site and therefore primes both the secreted and membrane-bound forms of ε mRNA and DNA. After sufficient amplification, the two populations of DNA fragments are resolved by gel electrophoresis. The secreted form of the ε chain can be distinguished by its reactivity with probe B. The purified DNA's are then subjected to DNA sequencing.

PCR amplification seems to be a more efficient procedure than cDNA cloning, because mRNA encoding the migis-ε peptide is poorly represented in the poly A+ RNA pool. The U266 ε chain cDNA (U266 being the parent cell line of SKO-007 with the same mRNA and cDNA) can be used to work out some preliminary annealing conditions between template DNA and oligo-primers.

Another approach for obtaining a DNA clone containing genes encoding the membrane-bound segments is to screen the human genomic DNA library. A preferred source for this human genomic library is constructed using human lung fibroblast W138 cells provided by Stratagene (La Jolla, Calif.). The genes are in lambda vector and the inserted DNAs have average sizes of 15K bp. Identification of the clones can be achieved by hybridization with U266 ε chain cDNA. The location of the gene segment corresponding to the membrane anchoring peptide can be determined by using a probe prepared from the homologous mouse gene of the transmembrane segment. The sequence of the gene segment encoding the membrane anchoring peptide is then determined.

3A. The Nucleotide Sequence of DNA Encoding the Membrane Anchoring Peptide of Human ε Chain The nucleotide sequence of genomic DNA encompassing the encoding segments for the membrane anchoring peptide of human membrane bound ε chain was determined by screening the human genomic library as described above. The sequences of Isoforms I, II and III are shown respectively in SEQ ID NO:1, SEQ ID NO:2, and SEQ ID NO:3, along with the deduced amino acid sequences for portions of the membrane anchoring peptide. The assignment of the exons was made by identifying the nucleotides for splicing donors and acceptors and by comparison to the published homologous sequences of mouse membrane-bound ε chain and of immunoglobulins of other classes.

For isoform I, the migis peptide is identified as the first fifteen amino acids encoded by membrane exon I, as indicated by the bold-faced amino acids in SEQ ID NO:1. This precedes a stretch of about 25 hydrophobic amino acids (underlined in FIG. SEQ ID NO:1) which form the transmembrane region. The migis peptide (Isoform I), as shown in SEQ ID NO:1, can exist in either of two structures. The first structure is a peptide monomer, with a structure as shown in SEQ ID NO:1. The second possible structure is a dimer, where two of the monomers shown in SEQ ID NO:1 are joined by a disulfide bond between each of their respective cysteine residues.

3B. The Nucleotide Sequence of DNA Encoding Various Isoforms of Membrane Anchoring Peptide of Human ε Chain U.S. Pat. No. 5,091,313 describes how to determine the nucleotide and amino acid sequences of the antigenic epitopes located on the extracellular segment of the membrane-bound region of the human ε chain. These epitopes are designated as the ε.mb/ec epitopes. Several approaches are possible, including starting with a mRNA preparation of a human myeloma cell line which expresses IgE on the surface. The mRNA can be used in establishing a cDNA library which is then screened with DNA probes for the transmembrane region gene segment of ε chain region.

An alternative approach, also described in U.S. Pat. No. 5,091,313, is to use PCR technology to successively amplify and purify the DNA sequence of the ε transmembrane region. The DNA is then sequenced.

Another alternative approach described in U.S. Pat. No. 5,091,313 is to screen the human genomic library. The gene segment corresponding to the membrane bound region can be determined with a probe prepared from the homologous mouse gene of the transmembrane segment, and the sequence of this segment is then determined.

In the present invention, the initial nucleotide sequencing was performed on the cDNA derived from mRNA isolated from human cells expressing membrane-bound IgE. A commercially available human IgE expressing myeloma, SKO-007 (from the American Type Culture Collection ("ATCC") Rockville, Md.), was used.

The DNA segments of cDNA regarded as pertinent to identification and characterization of the transmembrane regions of human ε chain were amplified by PCR, as described further below.

A. Construction of a Transfectoma Expressing Chimeric IgE.

Before proceeding to sequencing of the ε chain genome, a cell line secreting a hu/mu chimeric IgE and expressing membrane-bound IgE was generated to use in determining the reactivities of monoclonal antibodies with membrane-bound IgE on B cells. For constructing the chimeric ε and κ genes, the constant regions of human ε and κ genomic DNA and the variable regions of genomic DNAs of the heavy and light chains of a monoclonal antibody, BAT123 (specific for gp120 of HTLV-IIIB strain of HIV-1), were used. The variable region genes of BAT123 had been isolated from the functional heavy and light chain loci and used in the construction of murine/human (γ1/κ) fusion genes for the production of chimeric BAT123 (hu γ1/κ). See International Patent Application No. PCT/US88/01797; U.S. application Ser. No. 07/950,571. By replacing the human γ constant region with the ε constant region in the heavy chain expression vector, a chimeric BAT123 (hu ε, κ) with an antigen binding region derived from BAT123, was produced in a similar approach.

A λ phage clone containing the human germ line ε constant region was identified with a probe representing a segment of the constant domains (CH1-4) of ε chain. From this phage, a 6.4 kb DNA segment containing domains CH1 to CH4 and a 2.5 kb 3'-flanking sequence was subcloned into pUC19. By analogy to the reported mouse and rat ε-loci information, the presumed membrane exons were estimated to be located within the 1 Kb SacI fragment at the 3'-end of the ε gene. The 1 Kb SacI fragment was subcloned and sequenced to establish the presence of any membrane exon-like sequences.

The 6.4 kb DNA segment containing ε domains CH1 to CH4 and the membrane exons was linked to the BAT123 $V_H$ gene to give the chimeric mouse/human ε gene. This chimeric ε gene, together with the chimeric κ gene, were co-transfected into Sp2/0 cells by electroporation. The transfected cells were selected by the gpt and neo gene activities in the presence of mycophenolic acid and G418. The procedure was similar to that described in International Patent Application No. PCT/US88/01797 and U.S. application Ser. No. 07/950,571.

Stable transformants were established and analyzed for IgE secretion by ELISA, and for membrane IgE expression (by fluorescence flow cytometry). A clone, SE-44 was chosen for further studies. The cumulative IgE concentration in the culture supernatant of the SE-44 cells at $10^6$/ml was established to be 40 μg/ml.

To test for Ig expression on the cell surface by fluorescence flow cytometry, cells were incubated with anti-human IgE antibody, and developed with fluorescein labeled goat (Fab')$_2$ anti-mouse IgG. Cells Sp2/0, SKO-007, and chimeric IgE expressing cells were then fixed in 1% paraformaldehyde and analyzed on a Coulter EPICS flow cytometer. Fluorescence profiles for Sp2/0, SKO-007, and chimeric IgE expressing cells, respectively, were also run in the absence of primary staining antibody. Cell surface staining by anti-human IgE was estimated to be 60% and 50% for SE-44 and SKO-007 cells, respectively.

To further confirm that SE-44 cells express both membrane exons 1 and 2, the 1 kb SacI segment was separated into three portions utilizing the restriction enzyme ApaI. The two 250 bp fragments containing membrane exon 1 and its 5'-flanking region were used as the probe specific for exon 1. The 400 bp fragment containing exon 2 and the 3'-untranslated region was used as the exon 2 probe. These probes were used separately in Northern analyses to hybridize with cytoplasmic RNAs. Both probes yielded similar results and lit up messages of 3,000 and 3,600 nucleotides in length for SE-44 and SKO-007, respectively. The observation that SE-44 cells expressed shorter membrane-IgE messages than SKO-007 cells was expected. Since there is no termination/polyadenylation (t/pA) signals within the 1 kb SacI fragment, the chimeric ε gene used the SV40-derived t/pA signal present in the gpt gene construct for expression. The SKO-007 membrane IgE messages probably represent the normal intact transcripts using the endogenous ε-locus t/pA signal which is located 600 bp (estimation based on the size difference of the two messages) downstream from the 3'-end of the 1 kb SacI fragment. Northern analysis therefore suggests that both exons 1 and 2 are transcribed in these cells.

An identical Northern blot was also hybridized with the ε (CH1-4 domains) probe. Transcripts of approximately 2,300 nucleotides in length were noted for both SE-44 and SKO-007, in addition to weak bands characteristic for membrane IgE-specific messages.

Binding inhibition assays were used to demonstrate that the chimeric BAT123 (human ε,κ) bound to gp120 with an affinity constant comparable to that of BAT123 or chimeric BAT123 (hu γ1, κ). In experiments examining the binding of BAT123-HRP conjugate to solid phase gp120 in competition with BAT123 itself, chimeric BAT123 (hu γ1, κ), and chimeric BAT123 (hu ε1, κ) the replacement of mouse C γ1 in BAT123 with human C γ1 or human ε did not affect its antigen-binding affinity significantly.

B. Cloning and nucleotide sequencing of cDNA segments encoding the transmembrane region of human ε immunoglobulin.

In addition to SE-44, the cell line SKO-007, which also expresses human ε chain on its cell surface and which is a subclone of U266, was obtained from the ATCC. U266 was a myeloma cell line established from a blood sample of a myeloma patient.

Total RNA was extracted in guanidinium thiocyanate from $5 \times 10^7$ SKO-007 or SE-44 cells. The first strand cDNA was synthesized by AMV reverse transcriptase (Life Sciences, Inc., Petersburg, Fla.) according to the procedure described by the manufacturer.

The mRNA was reverse-transcribed using the oligo-dT primer into cDNA, which was then used as the template in PCR to amplify the pertinent segments covering the 3' end of the CH4 exon and the membrane exons. Several oligonucleotide primers, with the sequences as shown in SEQ ID NOS: 4-9, were used in the PCR. With respect to SEQ ID NOS:5, 7 and 9, it is noted that a complementary strand was used in the PCR. The underlined sequence in SEQ ID NOS:4-9 are the introduced EcoRI sites, for use in other studies.

The major products derived from PCR were either subjected to direct sequencing or cloned into a Bluescript II vector. The nucleotide sequences were determined for several clones derived from each individual band. The electrophoretic patterns of the PCR products and the sequencing data indicated unexpectedly the existence in both SKO-007 and SE44 cells of RNA species other than the one derived from the splicing of CH4 domain to the previously predicted me.1 and me.2 exons. When primers of SEQ ID NO:4 and SEQ ID NO:5 were used, the dominant PCR product was a segment originating from th direct RNA splicing of CH4 domain to me.2, using the predicted donor and acceptor sites, leaving out the me.1 domain. When these first-round PCR products were used as the template for a second round PCR using primers with the sequence as shown in SEQ ID NO:6 and SEQ ID NO:7, two major products were observed (SEQ ID NO:1 and SEQ ID NO:2) one originated from the splicing of CH4 domain to me.1 using the predicted donor and acceptor sites and the other was from the splicing of CH4 to a previously unidentified acceptor site 156 bp 5' of me.1 (the segment between this acceptor site and me.1 is referred to as me.p). However, when primers with the sequence as shown in SEQ ID NO:6 and SEQ ID NO:7 were used on cDNA as the template (first round PCR), the dominant product was a segment resulting from the splicing of CH4 domain to me.p (SEQ ID NO:3).

Additional PCR experiments using other pairs of primers also substantiate the observation of splicing from CH4 to me.p. When primers with the sequence of SEQ ID NOS:6 and 9 were used, the major product revealed the splicing of CH4 domain to me.p, resulting in the generation of combined me.p and me.1 segments (called me.1' domain). When primers with the sequence of SEQ ID NOS:8 and 5 were used, the splicing of the earlier predicted donor site at the 3' end of me.1 and the acceptor site at the 5' end of me.2 was established. So far, no other splicing combination has been found. Thus, these analyses revealed at least three forms of mRNA's of ε chain derived from the alternative splicings in the gene segment encoding the membrane peptide: isoform I contains CH4-me.1-me.2; isoform II contains CH4-me.1'(me.p+me.1)-me.2; isoform III contains CH4-me.2'.

C. Analysis of ε mRNAs by Northern blotting methods

Experiments were also carried out to identify the specific mRNA species in the RNA preparations from SKO-007 and SE44 cells by mRNA/DNA hybridization methods. $^{32}P$-labeled probes with sequences complementary to mRNA encoded in me.p, me.1, and me.2 segments were prepared by PCR and employed in Northern hybridization analyses for examining the presence of RNA species containing the represented segments. All these three probes were shown to hybridize with the mRNA from both cell lines on the Nylon membrane. The ε mRNA species detected in SE44 cells were all smaller than the corresponding species in SKO-007 cells.

Because isoform III was resolved from isoform I and/or II in the electrophoretic gel, the me.2 probe revealed two bands, one with and one without me.1' (or me.1) exon. On the other hand, because the me.1 probe could hybridize with both isoforms I and II, which were not resolvable in the gel, the Northern blotting analysis did not establish the presence of isoform I mRNA. In summary, the analyses with me.p and me.2 probes suggest convincingly the presence of mRNA's of isoforms II and III. In addition, the intensity of bands also suggest that the amounts of mRNA's of these isoforms and their relative proportions are different in SKO-007 and SE44 cells. The results with me.p and me.1 probes indicate the SKO-007 cells have more isoforms I/II (combined) than SE44 cells. The results with me.2 probe suggest that SKO-007 cells have comparable amounts of isoforms I/II and isoform III, while SE44 cells have more isoform III than isoforms I/II.

D. Predicted amino acid sequences corresponding to me.p and me.2' segments

Based on the nucleotide sequences of the PCR-amplified segments, the corresponding amino acid sequences for isoforms II and III were deduced and compared to that of isoform I. The reading frame of isoform II is the same as isoform I. The extra 52 a.a. (bold-faced in SEQ ID NO:2) lengthens the extracellular segment of the membrane-anchor peptide to a total of 67 amino acids from 15 amino acids in isoform I (SEQ ID NO:1). The omission of the me.1 (length 122 bp, not a multiple of 3) causes the reading frame of me.2' segment in isoform III to be shifted (SEQ ID NO:3); the peptide coding sequence is lengthened from 81 bp (encoding 27 amino acids) to 134 bp (encoding 45 amino acids).

The corresponding peptide of isoform III (SEQ ID NO:3) does not contain the hydrophobic stretch of 25 amino acids thought to span the membrane lipid bilayer (the segment is encoded by me.1). This suggests that it is secreted, and is not membrane-bound.

4. Developing Antibodies to the migis Peptides

Peptides containing any of isoforms I, II or III, or segments or immunologic equivalents of these peptides, can be used as immunogens. Polymers based on the immunogenic peptides can also be used, where the immunogenic peptide amino acid sequences, or equivalent sequences, are the polymer repeat unit. Immunogenic peptides based on isoform I may be in either the monomeric or dimeric form shown above. Immunogenic peptides based on isoform II may be in either the monomeric or dimerized form.

Such immunogenic peptides (designated herein as the peptides of the invention) can be synthesized by conventional techniques, such as with the RaMPS system (DuPont DeNemours & Co.), which applies Fmoc chemistry. Alternatively, recombinant peptides or immunoglobulin heavy chains (or portions thereof) containing isoforms I, II, or III may be biosynthesized by expressing in E. coli or eukaryotic cells the gene segments containing the coding sequence of these peptides.

When using a synthetic peptide segment as an immunogen, it is usually more effective to conjugate it to a protein carrier, for example, hepatitis B surface antigen, core antigen, or preferably keyhole limpet hemocyanin (KLH). If the peptidic segment lacks a lysine residue or if the lysine residue is in the middle part of the segment, it is desirable to add a lysine residue at the C-terminal end. Because the N-terminus already has an α-amino group, the modified synthetic peptidic will have two available amino groups for linking.

Multiple molecules of peptides can be conjugated to each molecule of the carrier protein. With KLH, a preferred molar ratio for peptide/KLH is 10. The method of conjugation is very well established. Crosslinkers such as glutaraldehyde or bis (sulfosuccinimidyl) suberate or preferably disulfosuccinimidyl tartrate (Catalogue #21579, 20591, Pierce Chemical Co., Rockford, Ill.) can be used.

As immunogens, these peptides can be used to make monoclonal antibodies which are specific for them, using the protocol described further below. Specific examples of making monoclonal antibodies to the migis epitope of human ε chain appear below and in priority U.S. Patent application Ser. No. 07/468,766, filed on Jan. 23, 1990.

The immunogenic peptides of the invention can also be used to immunize rabbits, goats, rats, or mice (or even another human being) to prepare polyclonal antibodies to the extracellular migis-ε epitopes. Monoclonal antibodies that react with the peptides of the invention can be further screened for positive specific reactivity with cells bearing a specific isotype. The monoclonal antibodies can then be applied in vivo. Polyclonal antibodies made against peptides of the invention, however, generally contain almost entirely antibodies that react with the synthetic peptide but not the native molecules. Whether the polyclonal antibodies made against synthetic peptides can react with intact cells must be tested.

When preparing monoclonal antibodies, it is not necessary to use the synthetic or recombinant peptides in both immunization and antibody identification. For example, in immunizing mice for preparing spleen cells for fusion with myeloma cells, the immunogen may be the membrane-bound immunoglobulin isolated from the plasma membrane of immunoglobulin-bearing myeloma cells, such as the IgG-expressing IM-9 cell line, or it may be the myeloma cells themselves. Transfectomas, which are developed by transfecting mouse myeloma cells with genes of human immunoglobulin heavy chains and light chains and which express on their cell surface membrane-bound immunoglobulins, may also be used as immunogens.

Lymphocytes from the spleen or lymph nodes of immune mice and rats can also be used to prepare hybridomas secreting monoclonal antibodies specific for the extracellular migis-ε epitopes. A preferred fusion protocol is to fuse immune spleen cells of mice with non-secreting mouse myeloma cells, such as NS-1 or Sp2/0 cells, using polyethylene glycol.

A preferred immunization protocol for preparing monoclonal antibodies is to inject into each mouse 50 μg of the conjugate of KLH and the recombinant or synthetic peptides of the invention in complete Freund's adjuvant. Two and four weeks later, the same amount of antigen is given subcutaneously in incomplete Freund's adjuvant. After about six weeks, the fourth antigen injection is given intraperitoneally in saline. Mice are sacrificed 4 days after the last injection and the spleens are removed for preparing single cell suspensions for fusion with myeloma cells.

A similar protocol can be used for immunization with purified native human membrane-bound immunoglobulins (having attached membrane anchoring peptide segments) isolated from the plasma membrane of immunoglobulin-bearing human myeloma cells, such as IM-9 cells. When human immunoglobulin-bearing cells are used as the immunogen, $1 \times 10^7$ cells are injected intraperitoneally at two week intervals.

The fusion procedure with polyethylene glycol and other various procedures concerning cloning and hybridoma culturing have been well established. The preferred fusion procedure is the well-known one described by Hudson, L. and Hay, F. C. (Practical Immunology, 2nd edition, pp. 303-313, 1980, Blackwell Publishing Co., Boston).

The screening of hybridomas for monoclonal antibodies (or the identification of polyclonal antibodies) reactive with the extracellular migis-ε epitopes can be performed with an enzyme-linked immunosorbent assay (ELISA) using the synthetic peptide as the solid phase antigen. A preferred solid phase antigen is the conjugate of a peptide of the invention with a carrier protein different from that used in the immunogen, such as bovine serum albumin or ovalbumin. Monoclonal antibodies specific for a particular peptide of the invention (corresponding to one of the isoforms) can then be screened for specific binding to B cell lines and B cells expressing that isoform by using immunofluorescence flow cytometric analyses.

Generally, the migis-ε epitope-specific monoclonal antibodies which are first obtained will be murine-derived, and thus may be immunogenic or allergenic in human therapy. It is therefore desirable to produce chimeric antibodies (having an animal variable region and a human constant region), or to use human expression vectors (Stratagene Corp., La Jolla, Calif.) to produce fragments of human antibodies ($V_H$, $V_L$, $F_V$, Fd, Fab, or $F(ab')_2$) and then construct whole human antibodies using techniques similar to those for producing chimeric antibodies. In addition, one can create antibodies in which the entire constant portion and most of the variable region are human-derived, and only the antigen binding site is derived from some other mammal. See Riechmann, L. et al., Nature 332:323-327 (1988). Further, one can create single peptide chain antibodies in which the heavy and light chain $F_v$ regions are connected. See Huston, J. S. et al., Proc. Natl. Acad. Sci. USA 85:5879-5883 (1983). All of the wholly and partially human antibodies are less immunogenic than mammalian equivalents, and the fragments and single chain antibodies are less immunogenic than whole antibodies. All these antibodies (which are among the antibodies of the invention) are therefore less likely to evoke an immune or allergic response. It is noted that an immune response could deplete the antibodies which are administered before such antibodies could function to suppress the immune response.

The antibodies of the invention can be used to reduce or eliminate the B cells expressing IgE by antibody-dependent cellular cytotoxicity (ADCC), complement-mediated cytolysis, or other cytolytic or regulatory immune mechanisms. For example, antibodies of certain IgG subclasses, such as mouse $IgG_{2a}$ and human $IgG_1$ and $IgG_3$, can mediate ADCC carried out by certain Fc receptor-bearing phagocytic leukocytes. Administration of such mouse $IgG_{2a}$ antibodies, chimeric antibodies bearing human γ-1 or γ-3 chains, or human $IgG_1$ or $IgG_3$ antibodies can be used to down-regulate or lyse B cells expressing IgE. These antibodies will not bind to the secreted form of IgE or to IgE bound to the surface of basophils or mast cells.

The antibodies of the invention can also be used as carrier agents of cytotoxic drugs or for delivering an effector substance, by conjugating the mAbs to these substances. A toxin-antibody conjugate will bind and directly kill B cells producing IgE, but not B cells producing other isotypes. These toxins are cytolytic or cytotoxic agents, including cytotoxic steroids, gelonin, abrin, ricin, Pseudomonas toxin, diphtheria toxin, pokeweed antiviral peptide, tricathecums, radioactive nuclides, and membrane-lytic enzymes (such as phospholipase).

The antibody and the agent can be conjugated by chemical or by genetic engineering techniques. The toxin-antibody conjugates may be used alone or in combination with the free antibodies of the invention.

The antibodies of the invention (and the toxin conjugates, fragments, and other derivatives) are administered systemically, and preferably intravenously. They can be administered in any pharmaceutically acceptable vehicle. The dosage to be administered can be arrived at from the known value of the approximate amount of IgE-bearing B cells in the body. Enough antibody is administered to entirely deplete the IgE-bearing B cells.

Another therapeutic alternative involves active immunization, wherein antibodies specific to the migis-ε epitopes are endogenously produced in vivo. These endogenously produced antibodies bind the migis-ε epitopes and cause destruction of the associated B cells. Production of such antibodies can be induced either by administering an immunogenic migis peptide of the invention, or a paratope-specific, anti-idiotypic antibody. Anti-idiotype antibodies against the paratope of the antibodies of the invention bear the internal image of the migis-ε epitopes. These anti-idiotypic antibodies can be used to actively immunize against the migis-ε epitopes and induce the endogenous formation of antibodies against the migis-ε epitopes. Such paratope-specific, anti-idiotypic antibodies are administered to a patient in an immunogenic amount sufficient to induce the formation of antibodies against B cells expressing IgE. These anti-idiotypic antibodies are preferably administered as chimeric antibodies or human antibodies, to minimize any immune response against them. They may also be any of the antibody fragments, $V_H$, $V_L$, $F_V$, Fd, Fab, or $F(ab')_2$ (which also may be chimeric or human in nature).

Certain factors, such as granulocyte monocyte-colony stimulating factor (GM-CSF) or monocyte-colony stimulating factor (M-CSF), are known to induce the proliferation of leukocytes, including those mediating ADCC. In in vitro experiments, GM-CSF and M-CSF have been shown to augment the ADCC activity on tumor cells mediated by monoclonal antibodies specific for surface antigens expressed on the tumor cells. The therapeutic effect of specific monoclonal antibodies of the invention, conjugates, or polyclonal antibodies in depleting IgE-expressing B cells could perhaps be enhanced by combining them with factors that augment ADCC activities.

Derivative antibodies can be made which draw cytotoxic cells such as macrophages or cytotoxic T cells toward the targeted immunoglobulin-expressing B cells. These derivative antibodies include bi-specific antibodies having a specificity for a receptor of a cytotoxic cell and a specificity for the targeted IgE-expressing B cells. Such hybrid bi-specific antibodies can include two different Fab moieties, one Fab moiety having antigen specificity for the targeted migis-ε epitopes, and the other Fab moiety having antigen specificity for a surface antigen of a cytotoxic cell, such as CD3 or CD8. The bi-specific antibodies of the invention can be a single antibody having two specificities, or a heteroaggregate of two or more antibodies or antibody fragments. See, e.g., C. Reading, U.S. Pat. Nos. 4,474,893 and 4,714,681; Segal et al., U.S. Pat. No. 4,676,980.

While monoclonal antibodies of the invention can be used for in vivo applications, they may also be used in extra-corporal ex-vivo applications. The IgE-bearing B cells in the circulation of the patients can be removed by an affinity matrix (antibody immobilized on a solid phase) which is conjugated with the monoclonal antibodies of the invention.

Another use for the antibodies of the invention is for determining numbers and relative proportions of B lymphocytes bearing particular isotypes in mixed leukocyte populations. The migis-ε specific antibodies will not react with cells which bear secreted immunoglobulins via such cells' Fc receptors. Such cells include macrophage and activated T cells. The profile of the B cells may indicate the allergic status of the individual, and whether further depletion of IgE-bearing B cells is desirable. The same information can also indicate how much antibody is needed to deplete a substantial portion of B cells bearing IgE. For this purpose, antibodies can be used in standard assays which are used to determine cell surface antigens. In general, the antibodies are contacted with a sample of the leukocytes to be tested under conditions which allow the antibodies to bind IgE-bearing cells in the sample. The cells are then examined for binding of antibody. This can be accomplished by conventional cell staining procedures, for example, a fluorescently labeled second antibody can be used to detect binding of antibody.

The monoclonals (or polyclonals) can also be further characterized. An immunofluorescence assay could be used to determine whether the antibodies of the invention bind to basophils. An immunofluorescence assay could also be used to determine whether the antibodies bind to mast cells, and to determine whether the antibodies of the invention react with SKO-007 myeloma cells, IgE-bearing B cells, and transfectomas expressing human/murine chimeric IgE. The results for the HEM7 mAb to isoform I are shown below in Table 4. An ELISA is used to determine reactivity with synthetic migis-ε peptides and with soluble IgE.

TABLE 4

| The Reactivity of Antibodies Specific for migis-ε Peptide with Different IgE-Containing Targets. | | |
|---|---|---|
| | Reactivity | Assays |
| Synthetic migis-ε peptide | + | ELISA |
| Soluble IgE | − | ELISA |
| SKO-007 myeloma cells | + | Immunofluorescence staining |

5. Experiments with Animal Models.

The substances and methods of the invention are likely to be tested on animal model systems. Two of the most relevant systems are the following.

A. Asthma/Rhesus Monkey Model

The monoclonal antibodies specific for human migis peptides and their related substances of this invention (some of which are described further below) are intended for use to treat patients with various IgE-mediated allergies (see section 6 below). Among these allergies, extrinsic asthma is a more serious form. An experimental model system for studying asthma has been established in rhesus monkeys.

A small portion of rhesus monkeys, which have been infected with the nematode *Ascaris suum*, develops sensitivity to extract of ascaris. When these sensitive monkeys are given spray continuing ascaris antigen, they develop breathing problems resembling asthma. Patterson, R., *J. Clini. Invest.* 57:586–593 (1976).

The various substances of this invention can be tested in the asthma/rhesus monkey model system. The ascaris sensitive monkeys are given the experimental treatment or control treatment and measurements are made to determine:

(a) Do the asthma symptoms upon ascaris challenge decline?

(b) Does the circulating IgE decline?

(c) Do the circulating IgE-bearing B cells decline?

(d) Does the IgE density on basophils decline?

B. Mouse model system

Mice are not known to develop allergic symptoms naturally. However, for demonstrating the pharmacologic mechanisms of the intended therapy by depleting IgE-bearing B cells and IgE, the mouse can serve as an excellent model.

The extracellular mouse ε chain migis peptide has already been sequenced. Ishida, N. et al., EMBO J. 1:1117-1123 (1982) and determined to have 19 amino acid residues. This peptide is synthesized in several forms, including one that has extra Leu-Lys residues at the C-terminus.

The peptide and its KLH conjugate are used as antigens to immunize rabbits and goats. The antisera are collected. The antigen-specific antibodies are purified using a column of Sepharose 4B conjugated with the peptide (with Leu-Lys addition) or with peptide linked to bovine serum albumin. Normal mice are injected intravenously (i.v.) or intraperitoneally (i.p.) with the purified antibodies (or their related substances), with the peptide (with Leu-Lys addition), or with peptide linked to bovine serum albumin. The mice are preferably immunized with the mouse migis-ε peptide conjugated to a carrier protein, such as keyhole limpet hemocyanin. After the treatments, the mice may also be challenged by infection with a parasite, *Nippostrongylus brasiliensis*, which is known to induce large quantities of IgE. Snapper, C. M. et al., *Immunol. Rev.* 102:51-75 (1988). The questions to be addressed include the following:

(a) Does the total IgE in circulation decline?

(b) Does the number of IgE-bearing B cells decline?

(c) Does the density of IgE on the surface of basophils decline?

(d) Do IgM and IgG specific for the mouse migis-ε peptide cause different effects? The purpose of this test is to determine the effect of ADCC on the depletion of IgE-bearing B cells. IgG, but not IgM, is known to mediate ADCC.

6. Therapy of IgE-Mediated Allergy Based upon the Selective Elimination of IgE-Producing Cells.

Antibodies specific for the migis-ε epitopes bind IgE on the surface of IgE-producing B cells and not on basophils and mast cells. This differential binding of IgE-bearing cell types provides the basis for therapeutic uses of the antibodies.

Conventional anti-IgE antibody will bind IgE on the surface of mast cells and basophils and trigger the release of pharmacological mediators of allergy. To be effective in therapy, the antibodies of this invention cannot bind IgE on these cells.

The antibodies specific for migis-ε epitopes can be used to treat IgE-mediated allergies in humans or other mammals (e.g. dogs, cats and horses). The antibodies can be used therapeutically in several ways, including as effector agents mediating an immune function, as carrier agents of toxins or cytotoxic drugs, for delivering an effector substance, or as targeting agents for cytotoxic cells.

A. Antibodies specific for IgE-producing cells.

Antibodies of certain IgG subclasses, such as mouse IgG2a and human IgG1 and IgG3, can be used to reduce or eliminate the IgE-bearing B cells by ADCC, complement-mediated cytolysis, or other cytolytic or regulatory immune mechanisms. These antibodies can also be used as effector agents mediating an immune function or as targeting agents for cytotoxic cells. The antibodies can be systemically administered, preferably intravaneously, as free antibodies to patients afflicted with IgE-mediated allergy in amounts sufficient to eliminate substantially IgE-producing cells and consequently, to substantially eliminate IgE.

The antibodies can also be administered nasally. On the lining of the nasal channels and the respiratory tract are areas in which active mast cells are concentrated. The IgE-producing B cells and free IgE in the extravascular space of these tissues may have better access to the basophils and mast cells than IgE-producing B cells and IgE in other parts of the body. Nasal administration (e.g., by nasal spray) may be used to deliver relatively high concentrations of therapeutic antibodies into these areas and thus to achieve speedier and more effective results. The antibodies can also be administered ocularly.

The mAbs of the invention may be used therapeutically in humans, and related mAbs against corresponding migis epitopes may be used therapeutically in other mammals, such as dogs, cats and horses. For therapeutic uses in humans, the human or humanized antibodies (and fragments) including chimeric antibodies, are preferred. Human and humanized antibodies are less immunogenic in humans than non-human antibodies. Consequently, they are better suited for in vivo administration, especially when repeated or long term administration is necessary.

Immunotherapies employing the antibodies of this invention may be used in combination with conventional desensitization immunotherapy. For example, desensitization with allergen may be performed in conjunction with the administration of either anti-migis-ε antibodies or antibody-toxin conjugates discussed above to substantially eliminate IgE producing cells.

Desensitization induces IgG production against the allergen/immunogen. Inducing such IgG production may be most effective as an allergy therapy when IgE-producing B cells are substantially depleted. The combination of antibody and desensitization therapy is attractive because although the IgE-producing B cells may only be temporarily depleted (for a few weeks or months) by the anti-migis antibody, and will eventually re-populate, the desensitization effect may last much longer.

B. Immunotherapy Combining an migis-ε-Specific Antibody and a Factor Enhancing ADCC.

The therapeutic effect of migis-ε epitope-specific monoclonal antibodies, polyclonal antibodies or antibody-immunotoxin conjugates in treating allergies should be enhanced by combining antibody therapy with factors that augment ADCC activities, such as GM-CSF (granulocyte monocyte-colony stimulation factor) or M-CSF (monocyte-colony stimulation factor).

C. Immunotoxins Specific for IgE-Producing Cells.

Antibodies specific for a migis-ε epitope can be combined with one or more of the immunotoxins noted above, thereby forming an antibody-immunotoxin conjugate which specifically targets IgE-producing B cells. The immunotoxins may be used alone or in combination with free anti-migis antibodies.

D. Extracorporeal Treatment

While the migis-ε-specific monoclonal antibodies can be used for in vivo therapy they may also be used in extra-corporeal ex-vivo therapy. The IgE in the circulation of allergic patients can be removed by an affinity matrix (antibody immobilized on a solid phase) that is conjugated with the monoclonal antibodies of this invention. Because antibodies may leak out from the affinity column and enter into the circulation of the patient, the monoclonal antibodies of the invention are preferable to other antibodies that can induce histamine release from basophils and mast cells.

7. Diagnostic Uses

Another use for the antibodies of the invention which target isoforms I and II is for determining numbers and relative proportions of IgE-bearing B lymphocytes in mixed leukocyte populations. The migis specific antibodies which target isoforms I and II will not react with cells which bear secreted IgE via such cells' Fc receptors. Such cells include macrophages and activated T cells. The profile of the IgE-bearing B cells indicates the allergic status of the individual, or how much antibody is needed to deplete a substantial portion of B cells bearing a particular isotype, where some of those B cells are tumorous. For this purpose, antibodies can be used in standard assays which are used to determine cell surface antigens. In general, the antibodies are contacted with a sample of the leukocytes to be tested under conditions which allow the antibodies to bind IgE-bearing cells in the sample. The cells are then examined for binding of antibody. This can be accomplished by conventional cell staining procedures, for example, a fluorescently labeled second antibody can be used to detect binding of antibody.

Antibodies which target isoform III can be used in standard assay formats to determine the amount of isoform III in a body fluid sample. This could also be useful to indicate the allergic status of the individual, or how much antibody is needed to clear entirely the isoform III IgE in the body. Given that IgE mediates allergic reactions, a determination of the amount of isoform III is important to determining allergic status.

With respect to the peptides representing the various isoforms of the migis-ε segment, they can be used in immunization of mice or other host animals to make the antibodies (monoclonal or polyclonal) of the invention. For such immunization, these peptides would preferably be linked to a carrier molecule, such as keyhole limpet hemocyanin.

With respect to the nucleotides which encode these peptides, it is noted that they can be used to make the peptides. The DNA sequences would be inserted into appropriate host cells using conventional recombinant techniques, and the peptides would then be produced by the host cells. The peptides can be used to make the antibodies of the invention, which can, as noted above, be used diagnostically or therapeutically. It is also noted that the complementary nucleotides to the nucleotides encoding the peptides can be used to make the nucleotides encoding the peptides, with conventional recombinant techniques.

The invention is illustrated further by the following examples.

EXAMPLE I

CONFIRMING MONOCLONAL ANTIBODY REACTIVITY WITH MIGIS-ε EPITOPES

Two different mAbs to the migis-ε epitopes were prepared. The preparation procedures are described below.

A. Preparing Monoclonal Antibody E46-13-3

Monoclonal antibodies against an epitope unique to membrane-bound IgE but not secreted IgE (isoform I) were prepared by a standard procedure for preparing hybridomas, as described in the Detailed Description of the Invention. The immunogen for immunizing BALB/c mice was the above-described SE-44 transfectoma cells. The mice were injected intraperitoneally 3 times at 2 weeks intervals with $1 \times 10^7$ SE-44 cells that were treated with 1 mM mitomycin C for 30 minutes at 37° C. prior to injection.

For initial screening of fusion wells, the human migis-ε peptide SEQ ID NO:1, in dimerized form, was used as coating antigen for ELISA. The positive clones were characterized in additional assays with other peptides and SE-44 cells and control cell lines.

From the several thousand fusion wells resulting from two fusion experiments, one hybridoma clone E46-13-3 was found to have specificity for the migis-ε peptide (Table 5).

TABLE 5

Specific Binding of Monoclonal Antibody E46-13-3 to Human migis-ε Peptide in ELISA.

| Solid-phase antigen (2 μg/ml) | $A_{450}$ |
|---|---|
| migis-ε peptide - ovalbumin | 2.707 |
| HIV-1 peptide* - ovalbumin | 0.011 |
| migis-ε peptide - KLH | 2.773 |
| HIV-1 peptide - KLH | 0.002 |
| KLH | 0.005 |

*The HIV-1 peptide was a 15-mer peptide representing a segment of gp120 of HTLV-IIIB strain of HIV-1. This peptide is reactive with BAT123 monoclonal antibody.

E46-13-3 and other monoclonal antibodies were further analyzed for reactivities with SE-44 cells compared to various control cell lines, including Sp2/0, the parent cell line for the transfectoma SE-44. Included in the control was the IM-9 cell line, which expresses IgG and CD23 on the cell surface, and the DAKIKI cell line, which expresses IgA on its surface. The tests were carried out with flow cytometric analyses with FITC-goat-anti-mouse IgG using an EPICS system. The results (shown below in Table 6) show clearly that E46-13-3 stained SE-44 specifically.

TABLE 6

| | Live cell staining studies of E46-13-3. | | |
|---|---|---|---|
| Cells | E46-13-3 | Net percent positive cells Control Monoclonal antibody | Anti-IgE Monoclonal-antibody |
| SE44 | 39.5 | 58.1 (anti-IgE) | 58.1 |
| Sp2/0 | 2.6 | — | 3.6 |
| IM-9 | 1.4 | 85.1 (anti-IgG) | 0 |
| IM-9 coated with IgE | 0 | 84.3 (anti-IgG) | 60.6 |
| DAKIKI* | 1.1 | 82.0 (anti-IgA) | 0 |

*IM-9 is a human IgG-expressing lymphoblastoid cell line: DAKIKI is a human IgA-expressing lymphoblastoid cell line. Both were obtained from ATCC.

B. Preparing Monoclonal Antibody HEM7

The migis peptides of all five human immunoglobulin heavy chain isotypes (including migis-ε) with an additional C-terminal lysine residue were synthesized. Conjugates of these migis peptides with keyhole limpet hemocyanin (KLH;Sigma) or with ovalbumin (Sigma) were prepared by cross-linking 1 mg/ml each with 0.04% glutaraldehyde (Sigma) in phosphate buffered saline (PBS), pH 7.4, for 16 h at 4° C., and dialyzed to PBS. Under these conditions more than 90% of the peptide was cross-linked.

BALB/c mice were then immunized subcutaneously and intraperitoneally with 100 μg migis-ε-KLH in Freund's adjuvant 4 times and then intraperitoneally twice with mitomycin C (Sigma)-treated (20 mg/ml for 20 h) SE44 mouse myeloma cells (which express human IgE on the cell surface). Spleen cells were fused with Sp 2/0 cells using polyethylene glycol (Carbowax, Fisher). Supernantants of growing hybrids were screened in enzyme-linked immunosorbent assay (ELISA) for reactivity to migis-ε ovalbumin. Positive wells were then tested for ability to bind to cell surface IgE by indirect immunofluorescence flow cytometric analyses.

The HEM7 hybridoma secreted an antibody showing specificity in these assays and was subcloned by limiting dilution. Antibodies from culture supernatants were purified by protein A (Repligen)-affinity chromatography.

The purified mAb HEM7 was analyzed for specific binding to the migis-ε peptide and to mIgE. The migis peptides of the four other heavy chain isotypes (IgG, IgA, IgM, and IgD) were also synthesized and the reactivity of HEM7 with these peptides was examined. These migis peptides are at least 13 amino acids long and apparently hydrophilic, containing 6 or 7 acidic amino acids. The migis peptides show a great degree of heterogeneity; although migis-μ and migis-γ are the most homologous to migis-ε.

In the ELISA microtiter plates (Immulon 2, Dynatech) were coated at 1 μg/ml PBS with migis-ε peptide, and the migis-μ, migis-γ, migis-α, migis-δ peptides, as well as with migis-ε peptide-ovalbumin conjugate, or with human serum IgE (Ventrex), or other serum proteins (Jackson Immunoresearch), for 16 h at 22° C. Plates were post-coated with blocking buffer, containing 5% non-fat dry milk (Carnation), 0.05% Tween 20 (Sigma) in PBS for 1 h at 22° C. Binding of murine antibodies (1 h, 22° C.) was detected using peroxidase-conjugated goat anti-mouse IgG (Kirkegaard and Perry) and a tetramethyl benzidine (TMB) substrate solution containing 10 μg/ml TMB (Sigma) and 0.0036% $H_2O_2$, acidified with 0.7M $H_2SO_4$, and absorption at 450 nm was quantitated using an ELISA plate reader (Bio-Tek).

HEM7 was shown to bind to migis-ε peptide reaching maximal binding at 100 ng/ml antibody concentration. It did not bind to any measurable extent to the migis peptides of the other four isotypes. Furthermore, HEM7 even at 10 μg/ml did not bind to soluble, secreted IgE purified from human serum. Nor did it bind to IgE purified from supernatants of SE44 cells, or to other human Igs or serum substances (data not shown).

The purified HEM7 mAb was also tested for its ability to bind to IgE-bearing SKO-007 cells in immunofluorescence flow cytometric assays. The immunofluorescence flow cytometric assays were carried out as follows. Cultures of B cells secreting various human immunoglobulins and other human blood cell lines were obtained from the ATCC. Peripheral blood was obtained by venipuncture from adult volunteers and mononuclear cells were isolated using Ficoll-Paque (Pharmacia). Cultured cells were stained with antibodies and fluorescence quantitated by flow cytometry (EPICS-V, Coulter Diagnostics). Peripheral blood lymphocytes and monocytes were gated by their light scattering properties. Presence of surface markers was confirmed using mAb reagents specific for IgE(HP6029), IgG(HP 6046), IgM(HP6081), IgD(JA11), and IgA(2D7) (all from Zymed), and for other leukocyte surface markers (CD4, CD14, CD45 and CD23) (from Becton-Dickinson).

Inhibition of binding of HEM7 to SKO-007 cells by migis peptides was also assayed. These assays were performed by preincubating the mAb HEM7 or TES-19 (30 μg/ml) with migis peptides for 1 h on ice before cells were added to the mixture.

Maximal binding of HEM7 to SKO-007 cells could be achieved at 10-30 μg/ml. Furthermore, the binding of HEM7 to SKO-007 cells could be nearly completely inhibited by migis-ε peptide at 1 μg/ml, a concentration approximately equimolar to the antibody present. In contrast, the migis-γ peptide did not inhibit HEM7 binding substantially even at a 1000-fold higher concentration. Nor did the migis-ε peptide inhibit the binding of TES-19 mAb to SKO-007 cells.

HEM7 was also tested for its ability to bind to human cells bearing other surface Ig. Among the various human cell lines tested, HEM7 was able to bind to SKO-007 cells and to the related U266 cells that bear mIgE, but not to B cell lines expressing IgM, IgD, IgG, or IgA. The mAb also did not bind to any other cells tested, including a T cell line, a monocyte-like cell line, and peripheral blood mononuclear cells (Table 7).

TABLE 7

Reactivity of mAb HEM7 with various human cell types*

| Cell type | Surface marker | Positive cells (%) |
|---|---|---|
| SKO-007 (myeloma cell line) | IgE | 46 |
| U266B1 (myeloma cell line) | IgE | 22 |
| IM-9 (B lymphoblast line) | IgG | 0 |
| RPMI 1788 (B lymphoblast line) | IgM, IgD | 2 |
| DAKIKI (B lymphoblast line) | IgA | 0 |
| CCRF-CEM (T lymphoblast line) | CD4, FcγR | 0 |
| U-937 (Monocyte-like cell line) | | |
| Peripheral blood lymphocytes | CD23 | 0 |
| Peripheral blood monocytes | CD45 | 0 |
| | CD45, CD14 | 3 |

*The reactivity was quantitatively determined by indirect immunofluorescence staining employing flow cytometric methods as described above. The percents of positive cells were determined as the increase of percents of cells with fluorescence levels above a set threshold after incubation in HEM7 at 10 μg/ml, in comparison to the percents of these cells when a negative control mAb was used. Values shown are from one representative of three experiments. Values of <5% positive cells are within the variability of the assay.

The specific binding of HEM7 to mIgE was further examined by Western immunoblotting analyses using the plasma membrane fraction isolated from disrupted SKO-007 cells. The Western immunoblotting was carried out as follows.

Proteins in purified polyclonal human serum IgE (0.1 μg, Ventrex) and a plasma membrane fraction from SKO-007 cells (25 μg) were fractionated on 10% SDS-PAGE and electroblotted onto nitrocellulose. The filters were incubated with either peroxidase-conjugated polyclonal goat anti-human ε chain at 2.5 μg/ml, or with HEM7 at 25 μg/ml, followed by peroxidase-conjugated goat anti-mouse IgG, and TMB with membrane enhancer substrate (enzyme conjugated antibodies and substrate from Kirkegaard and Perry). M. W. markers were from BioRad.

Goat anti-human IgE ($\epsilon$ chain specific) revealed two bands in the area of about 80 kDa (M. W.); HEM7 reacted with only the higher M. W. band. These results suggest that the plasma membrane preparation was contaminated with secreted IgE, which was the lower M. W. (80 kDa), denser band stained by goat anti-human $\epsilon$ and that HEM7 reacted only with the membrane-bound form of $\epsilon$ chain, which has a higher M. W. (87 kDa) because it contains the extra membrane-anchoring segment. Again, the immunoblotting reaction of HEM7 with the specific protein in the nitrocellulose membrane could be inhibited by the migis-$\epsilon$ peptide. Immunoblots of polyclonal human serum-derived IgE showed no reactivity with HEM7 (column b), nor did immunoblots of plasma membrane fractions from a control cell line (IM-9) secreting IgG.

HEM7 was also checked to determine if it would cause histamine release from peripheral human blood basophils, which cells were taken from four individuals. Each assay was run using various concentrations of TES-17 mAb (a mAb specific for human IgE which induces histamine release from leukocytes) and HEM7. Polyclonal antibodies to human IgE (which also induce histamine release) served, in addition to TES-17, as an additional positive control. Goat anti-mouse IgG was added to some of the tests as an enhancer.

It was shown that HEM7 did not cause histamine release in a mAb dose-dependent fashion, irrespective of whether the enhancer was present.

EXAMPLE II

CONFIRMING THAT ISOFORM II EXISTS, IN VIVO, AND THAT IT IS MEMBRANE-BOUND

The predicted isoform II contains 52 additional amino acids between C$\epsilon$4 and the 15 amino acid segment bound by HEM7. Monoclonal and polyclonal antibodies were prepared to 36 amino acid synthetic peptide corresponding to residues 6 to 40 of the 52 amino acid segment. Both in ELISA and on immunoblots, the antibodies react with IgE from cell lysates but not with IgE from cell culture supernatants, suggesting that isoform II exists on cells and is not secreted. Moreover, on immunoblots, the 15 amino acid band recognized by HEM7 co-migrates with that recognized by the antibodies to the 36 amino acid segment.

EXAMPLE III

CONFIRMING THE IN VIVO EXISTENCE OF ISOFORM III mRNA AND PEPTIDE

A. Detecting $\epsilon_2$ mRNA in Human Lymphocytes by PCR

Experiments were conducted to ensure that isoform III mRNA was produced by human peripheral blood lymphocytes.

For the convenience of presentation, the predicted $\epsilon$ chain encoded by the mRNA with CH4-me.2' splicing (designated as isoform III above) is referred to below as $\epsilon_2$, and the conventional $\epsilon$ chain of secreted IgE (designated as isoform I above) is referred to as $\epsilon_1$. IgE molecules containing one or two $\epsilon_2$ chains are referred to as IgE$_2$, and IgE molecules containing only $\epsilon$ chains are IgE$_1$.

The PBMC from an allergic patient, whose serum IgE concentration was about 1 μg/ml (about 10–20 times average), were isolated and the total RNA from these cells was prepared. After the first strand cDNA template was generated, PCR was performed using a pair of primers, one of which was located in CH4 domain and the other in the me.2 domain. The PCR-amplified products were analyzed by gel electrophoresis and the DNA in the major bands were subcloned and their nucleotide sequences determined.

The major PCR product using the cDNA template derived from the RNA of SKO-007 and SE44 cells was a segment of $\epsilon_2$ mRNA. The same segment was also the major product with the cDNA from the human PBMC preparation. An autoradiograph showed that the $^{32}$P-labeled DNA probe corresponding to an me.2 segment hybridized with the $\epsilon_2$ segment. It also hybridized with two other bands, corresponding to two segments derived from two isoforms of membrane-bound $\epsilon$ chain mRNA. Nucleotide sequencing of DNA fragments cloned from these bands confirmed this conclusion.

B. Detecting $\epsilon_2$ Chains in Culture Medium of Human IgE-secreting Cell Lines A 33 amino acid peptide corresponding to a portion of the me.2' segment and an additional C-terminal lysine residue, was synthesized. The peptide had the sequence as shown in SEQ ID NO:10.

The peptide, designated the "E2T peptide," was conjugated to KLH and used to immunize mice, using a standard protocol described above. Monoclonal antibodies were made which bound to the E2T peptide specifically. These mAbs also bound to $\epsilon_2$, as determined on immunoblots.

The E2T peptide, conjugated to KLH, was also used to immunize rabbits. The resulting antibodies specific for E2T were affinity purified by a small column of agarose beads conjugated with E2T. This purified anti-E2T was conjugated with horseradish peroxidase and to agarose beads. These various reagents were then used in ELISA and immunoblotting assays to detect $\epsilon_2$ chain and IgE$_2$. In the ELISA with anti-E2T as the solid-phase immunoadsorbent and peroxidase-labelled goat antibodies against human IgE as the tracer, $\epsilon_2$ chain could be detected in the culture supernatant of SE44 cells, and to less extent, in that of SKO-007 cell. The substance was absent in the media of SP2/0 cells and of CAG1-51-4 cells.

Since the variable regions of the heavy and the light chains and the antigen specificity of the chimeric IgE ($\epsilon$, $\kappa$) secreted by SE44 cells and of the chimeric IgG ($\gamma$1, $\kappa$) secreted by CAG1-51-4 cells are identical, the binding of the $\epsilon_2$ chain or IgE$_2$ from the media of SE44 and SKO-007 cells to the solid phase was not due to the variable regions. The $\epsilon$ chain in the culture supernatant of SE44 cells did not bind to rabbit antibodies specific for an irrelevant antigen.

The possibility that anti-E2T could react with membrane-bound $\epsilon$ chain (designated as "$\epsilon_m$ chain") was examined by testing its binding to a recombinant $\epsilon_m$ chain. The recombinant $\epsilon_m$, which extended from CH2 domain to the membrane anchoring peptide, was produced in E. coli and purified by affinity column. An ELISA showed that mAb E11-4-70, which reacts with $\epsilon_1$ chain, and mAb HEM7, which is specific for the extracellular 15 a.a. segment of the membrane anchor peptide, reacted with the recombinant $\epsilon_m$, while anti-E2T did not. These results indicate that the cytoplasmic segment of $\epsilon_m$, which is encoded by the same exon as E2T but using a different reading frame, is not reactive with anti-E2T, and that the $\epsilon$ chain in the culture supernatant of SE44 cells, that was reactive with anti-E2T, was not $\epsilon_m$ possibly shed from the cellular plasma membrane.

C. Detection of IgE$_2$ by Western Blot Analyses and Affinity Adsorption

The IgE secreted by SE44 cells into the culture medium was affinity purified by a mAb, TES-61, which is presumed to be specific for CH domains of IgE. The purified IgE was gel electrophoresed with or without treatment of reducing agents, transblotted onto nitrocellulose filters, and reacted with various antibodies to be studied. In the blots transferred from a nonreducing gel, both horseradish peroxidase-conjugated goat anti-human IgE and anti-E2T stained a band of about 200 Kd, indicating that $\epsilon_2$ chain was present in IgE molecules and not as single chains. In addition, both in the reducing and nonreducing conditions, anti-E2T reacted with substances with M.W. at the higher end of those bands stained by goat anti-human IgE.

Equivalents

Those skilled in the art will recognize, or be able to ascertain using no more than routine experimentation, many equivalents to the specific embodiments of the invention described herein. Such equivalents are intended to be encompassed by the following claims.

---

I claim:
1. An isolated DNA or RNA fragment encoding the peptides of SEQ ID NO:2 or SEQ ID NO:3.

2. An isolated DNA or RNA fragment with the sequence of SEQ ID NO:2 or SEQ ID NO:3.

3. A peptide with the sequence of SEQ ID NO:2 or SEQ ID NO:3.

* * * * *